United States Patent [19]

Klein et al.

[11] 4,307,081

[45] * Dec. 22, 1981

[54] ENZYME MIXTURE

[75] Inventors: Gerold K. V. Klein, Merepoint Rd., Brunswick, Me. 04011; John C. Houck, Seattle, Wash.

[73] Assignee: Gerold K. V. Klein, Brunswick, Me.

[ * ] Notice: The portion of the term of this patent subsequent to Apr. 8, 1997, has been disclaimed.

[21] Appl. No.: 181,076

[22] Filed: Aug. 25, 1980

Related U.S. Application Data

[60] Division of Ser. No. 143,007, Apr. 23, 1980, which is a continuation-in-part of Ser. No. 45,109, Jun. 4, 1979, Pat. No. 4,226,854, which is a division of Ser. No. 887,607, Mar. 17, 1978, Pat. No. 4,197,291, which is a continuation of Ser. No. 678,695, Apr. 20, 1976, abandoned, which is a continuation-in-part of Ser. No. 489,254, Jul. 17, 1974, abandoned, which is a continuation of Ser. No. 431,622, Jan. 8, 1974, abandoned.

[51] Int. Cl.$^3$ ............................................. A61K 37/54
[52] U.S. Cl. ..................................................... 424/94
[58] Field of Search ................... 435/212, 219; 424/94

[56] References Cited

PUBLICATIONS

Levenson et al., "Chemical Debridement of Burns" in Annals of Surgery, vol. 180, Oct. 1974, pp. 670-704 (pp. 670, 673, 681, 693, 696-699, 702-704).

*Primary Examiner*—Lionel M. Shapiro
*Attorney, Agent, or Firm*—Wyatt, Gerber, Shoup, Scobey & Badie

[57] ABSTRACT

Disclosure relates to novel escharase containing proteolytic enzyme mixture derived from bromelain useful for the digestion, dissection and separation of non-viable, devitalized tissue, especially eschar tissue from viable tissue in a host organ.

7 Claims, 1 Drawing Figure

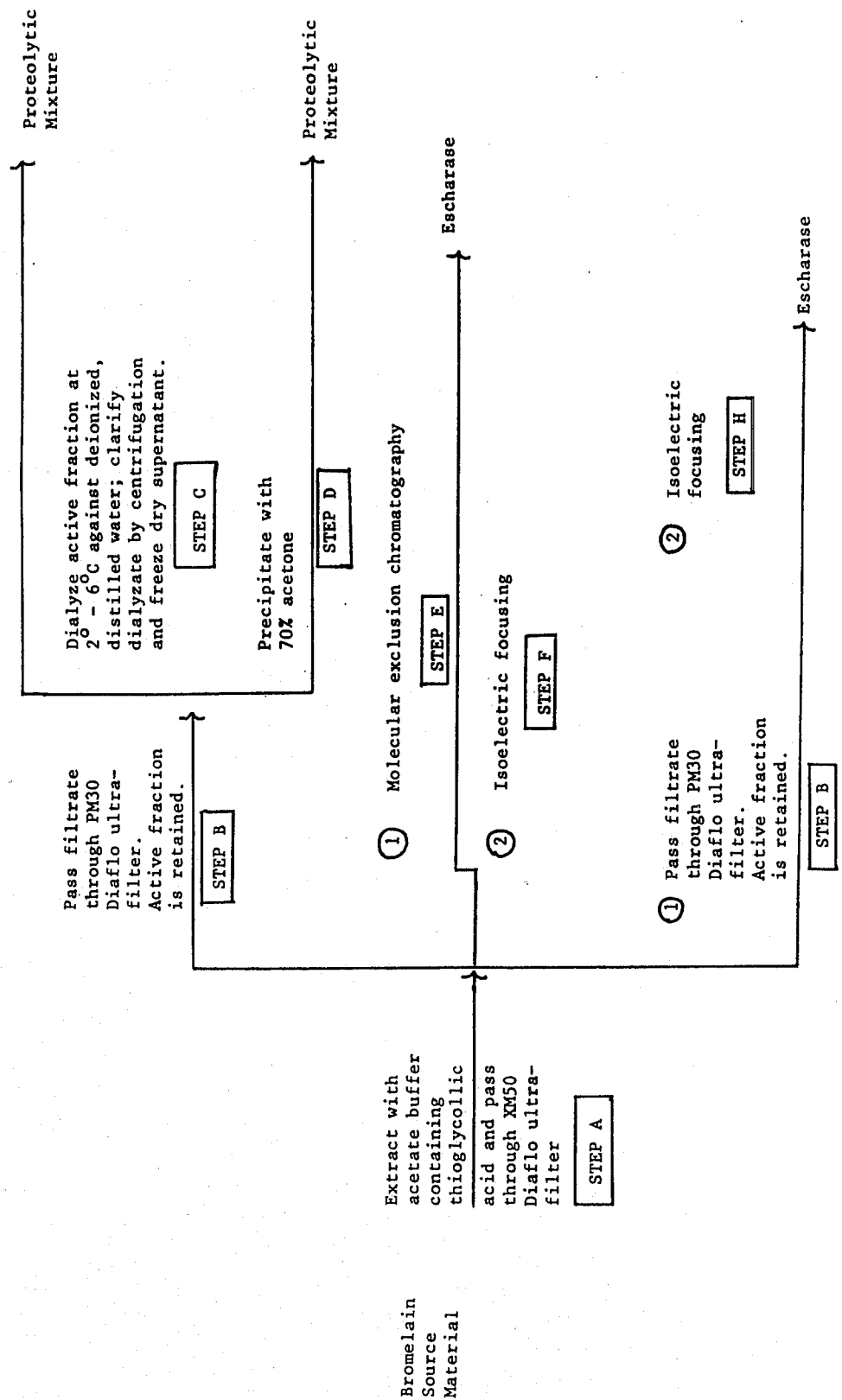

ENZYME MIXTURE

RELATED APPLICATIONS

This application is a division of Ser. No. 143,007 filed Apr. 23, 1980 which in turn is a continuation-in-part of copending application Ser. No. 045,109 filed June 4, 1979, U.S. Pat. No. 4,226,854, issued Oct. 7, 1980, which is a divisional of application Ser. No. 887,607 filed Mar. 17, 1978, U.S. Pat. No. 4,197,291, issued Apr. 8, 1980, which is a continuation of application Ser. No. 678,695 filed Apr. 20, 1976, now abandoned. This latter application is a continuation-in-part of application Ser. No. 489,254 filed July 17, 1974 which is a continuation of application Ser. No. 431,622 filed Jan. 8, 1974. Both of these last named applications are now abandoned.

BACKGROUND OF INVENTION

This invention relates to novel escharase containing proteolytic enzyme products, therapeutically useful compositions containing such materials, and to methods of utilizing such products especially in debridement of eschar tissue.

Considerable efforts have been made to discover materials capable of distinguishing between viable and non-viable tissue. The discovery of materials which would digest devitalized tissue while not attacking viable tissue would make it possible to remove the devitalized tissue without surgery. It would be a beneficial therapeutic agent in virtually all disease processes where topically devitalized tissue needs to be removed from the viable organism such as decubitus ulcers, pressure necroses, incisional traumatic and pyogenic wounds, and ulcers secondary to peripheral vascular disease.

One area that has attracted considerable attention is the use of proteolytic enzymes and other chemicals to effect the early debridement of eschar tissues resulting from burns. Such devitalized tissue is an excellent culture medium and the principal source of the septicemia which is the proximate cause of death in the majority of severely burned patients. Intensive investigations with such agents as tannic acid, salicylic acid, and pyruvic acid as well as papain, pinguinain, trypsin, streptokinase and other enzymes have not led to satisfactory results. Chemical agents such as tannic acid were found to cause further injury to already damaged tissue. Known proteolytic enzymes were found to be too slow, to have toxic side effects or to attach viable as well as devitalized tissue.

It is important that debridement of eschar tissue take place early, i.e. in a period which is preferably no longer than four days, and by an agent which effects debridement rapidly. If debridement is postponed for too extensive a period, there results septicemia from invasion of the wound by infectious microorganisms and toxemia from absorption by viable tissue of toxic degradation products from the devitalized tissue. Rapid debridement is essential since the environment normally utilized is one which serves as an ideal culture media for the growth of infectious colonies of microorganisms.

As a result, sharp, surgical debridement with its attendant pain and heavy bleeding continues to be the principal method for the removal of eschar.

The enzyme bromelain which is, in fact, a complex mixture containing materials including a number of hydrolytic and proteolytic enzymes has been used in the treatment of burns. In fact, hydrated bromelain powder and some crude extracts of bromelain have been employed previously for debridement of eschar tissue; see Journal of the Maine Medical Association, September 1964; Research in Burns, Han Huber, Publishers Bern Stuttgart Vienna 1971. These materials, however, have now proved to be satisfactory, principally because the results were not reproducible.

THE INVENTION

Novel hydrolytic enzyme materials useful therapeutically for dissection of devitalized tissues have not been discovered. The novel products of this invention can be employed for dissection and to facilitate removal of devitalized tissue from a mammalian host.

The products of this invention may be obtained by treatment of commercially available bromelain. In the presently preferred procedure for obtaining bromelain from the stem pf the pineapple plant, the juice from the stem is first adjusted to a pH of about 3 or 4 with phosphoric acid and sodium sulfhydride is added to protect against sulfhydryl oxidation. The inert material is precipitated at about 30% acetone (addition of sufficient acetone so that the solution is 30% in acetone) and, after filtration, the clarified fluid is precipitated with 70% acetone. This precipitate is collected by centrifugation and either redissolved in water containing sodium sulfhydride which has been acidified with phosphoric acid and reprecipitated, or dried in a vacuum oven directly. If the material is reprecipitated, 70% acetone is utilized. The dried material from either process is suitable as a starting material to obtain the products of this invention.

Either of these source materials is extracted (10 grams per 200 ml) in acetate buffer 0.1 M, pH 5.5 which has been made up to 1% in thioglycolic acid. The pH of this solution is approximately 4. The solution is expressed through XM 50 Amicon Diaflo ultrafilter (Amicon Corp., Boston, Mass.) and concentrated over PM 30 Diaflo filters. The active solution containing a mixture of proteolytic enzymes having molecular weights of from 30,000 to 50,000 dalton can be either dialyzed at 2° to 6° C. against deionized, distilled water (200 volumes), clarified by centrifugation, and the clear supernatant freeze dried; or the active fraction can be precipitated with 70% acetone. Both procedures produce the useful products of this invention.

The enzyme mixture thus obtained contains proteolytic enzymes and escharase. The escharase may be isolated by procedures described in more detail below. The mixture is useful because it is capable of rapidly digesting eschar tissue as well as the interfacial layer between the eschar and viable tissue to produce a graftable bed for the grafting of new tissue.

Because of the method of recovery, the molecular weight of the components of the enzyme mixture is apparently about 30,000 dalton, and the maximum molecular weight is apparently 50,000. This molecular weight is considerably in excess of any previously reported figures for bromelain. The product is clearly not bromelain because it did not oxidize on dialysis. This is a well known property of bromelain. The mixture also differs from other bromelain fractions which have been previously reported as useful for debridement. The most apparent difference is the fact that the novel products of this invention are water soluble. As a result, it is possible to utilize them in parenteral solutions for injection. Such water soluble solutions have been observed to be particularly useful to dissolve thrombi. For this utility, the products of this invention have marked advantages over streptokinase and urokinase, both of which have been previously utilized as thrombolytic agents since these latter proteolytic enzymes are very difficult to isolate and therefore very expensive.

Moreover, the molecular weight range of the products of this invention is such that pathogenic organisms which are known to be of much higher molecular weight are excluded. The products of the invention therefore are inherently sterile provided, of course, that they are prepared under sterile conditions.

It is clear that the enzyme fraction thus obtained is different from any previously reported materials. Moreover, unlike any previously reported materials it is safe, reliable and effective. The therapeutic results arising from its proper utilization are predictable and reproducible.

While we do not wish to be limited by theory, it appears that the products of this invention are capable of effecting reproducible results since they do not contain an inhibitor which was apparently present in previous preparations. This inhibitor restricted the proteolytic activity of the isolated fractions for devitalized tissue as a substrate. The products of the invention therefore are inhibitor free, in the sense that they do not contain a self-inhibitor which precludes proteolytic digestion of devitalized tissue. On the other hand, the proteolytic activity of the products of the invention is clearly inhibited by the presence of a factor in viable tissue since the products do not digest viable tissue. In this respect, they are clearly different from other proteolytic enzymes which have been recommended for the debridement of eschar tissue.

The enzyme mixture may be provided in two forms both of which are useful. The lyophilized product is generally less dense than the fraction obtained by acetone precipitation. Either fraction can be used alone or in conjunction with the usual pharmaceutically, acceptable excipients such as petrolatum, isotonic saline, polysaccharide gels or other stable, inert hydrocarbon bases. Such compositions should be prepared immediately prior to use since the products of the invention are not stable in the presence of moisture.

The enzyme mixtures obtained by the above described procedures are useful for the removal of eschar tissue thereby to produce graftable beds on burn victims. The products are characterized by the presence of escharase which appears to be principally responsible for the removal of the interfacial layer. They may be defined as escharase containing, heat labile, water soluble, proteolytic enzyme mixtures in which the molecular weight of the components is from about 30,000 to 50,000 daltons which are derived from bromelain and activated by moisture to dissect and digest devitalized tissue.

In certain situations, it may be desirable to add other active ingredients to the therapeutic compositions of the invention. For example, antibiotics may be added to control possible infection, or a keratolytic agent such as urea may be added to aid in the breakup of the eschar tissue.

Early laboratory experimentation with the enzyme mixture was carried out on surgically debrided eschar from a severely burned patient. The eschar was placed in test tubes and contacted with different concentrations of the product of the invention in isotonic saline solution at different temperatures and in atmospheres of different gases. The experimentation showed a rapid disruption on the continuity of the human eschar by the proteolytically active material at even the most dilute concentration such as 0.1% by weight. Good digestion was obtained at body temperature. The best activity was observed when the experimental mixture was blanketed with an inert gas to exclude oxygen.

Following the test tube experiments, the mixture was applied to experimental burns on piglets. In these experiments, it was found that exclusion of oxygen and activation by moisture were essential to the therapeutic utility of the proteolytic mixture.

Experimental full thickness burns were produced on anesthetized piglets by radiant heat. Six different piglets were tested. Each experimental burn was soaked with normal saline for periods of up to four hours after the passage of time indicated in the table below:

TABLE 1

| Post Burn Period | Duration of Saline Soak |
| --- | --- |
| 1 hour | 0 hour |
| 24 hour | 1 hour |
| 36 hour | 1.5 hour |
| 48 hour | 2 hour |
| 72 hour | 4 hour |

Each burn was punctured with a series of small holes to permit easy passage of the proteolytic activity through the eschar tissue to the underlying demarcation line between the eschar tissue and the viable tissue. The burns were then separately coated with the proteolytic powder of the invention and then with agar. The agar was coated with a plastic sheet, and the edges of the sheet were tightly adhered to the surrounding flesh to protect against the oxygen in the air. A small amount of normal saline is then injected through the plastic and into the agar. This moisture has two effects. It swells the agar to further protect the enzyme mixture from oxygen and it activates the enzyme.

The active powder was applied to the eschar tissue in a quantity of 0.1 mg/mm$^2$. The proteolytic composition was found to be effective in quantities as low as 0.1 mg/mm$^2$, but is preferably used in quantities up to 10 mg/mm$^2$, or even higher to insure contact of the enzyme with the nonviable tissue substrate.

At the end of about a one-hour period, the coverings were removed and it was found that the non-viable tissue could be removed from the viable tissue with minimal bleeding and with no apparent toxic effects. The bed of viable tissue remaining after removal of the eschar is suitable for acceptance of a graft.

The graft was applied to the experimental burns from which the eschar tissue was removed after first washing with hydrogen peroxide to neutralize remaining enzymatic activity, and then washing with normal saline. The grafts took successfully.

In a subsequent test with a human subject, a full thickness burn 5 cm$^2$ in area was formed on the skin surface of the anterior thigh under local anesthesia by exposure to radiant heat for thirty seconds at 360° Celsius. At the end of one hour, a paste formed from a 1:1 mixture of the escharase containing enzyme mixture of this invention in physiological saline solution was applied to the burn. The paste was covered with a transparent plastic sheet to seal out oxygen and to maintain humidity, and then with a pressure bandage to secure good contact between the burn substrate and the enzyme. The dressing was removed after one hour and the eschar tissue was found to be partially digested. There was no adherence to the wound bed, and the remains of the eschar tissue were completely removed by simple wiping, leaving a wound bed suitable for acceptance of a graft.

It was observed that even after the effects of the local anesthetic had subsided, there was no pain associated with the removal of the partially digested tissue, or any other manipulation of the wound bed. The bleeding was minimal.

The wound bed was covered with a split thickness autograft. The autograft was inspected after four days. It was found that the graft bed was almost fully covered. At the end of seven days, the wound bed was 100% covered with a viable skin autograft.

It has been observed that the enzyme mixture does not digest the eschar tissue appreciably under the conditions described above when exposure is of relatively short duration, for example, one hour. Rather, it disects the eschar tissue from the underlying tissue by clearing the interfacial connecting tissue. This reaction takes place extremely rapidly.

The rapid hydrolysis of the connecting tissue was illustrated by another experiment of the nature described above with a piglet having an experimental burn. The entire eschar and the surrounding tissue was covered with an adhesive plastic spray and then a small vertical hole about 1 mm in diameter and 5 mm deep was drilled in the center of the eschar. The hole is filled with a powdered product of the invention and then moistened with a few drops of saline colored with Evans Blue dye. Care was taken so that none of the enzymatic material spilled over the edges of the hole, and it was sealed with plastic. After one hour, bluish discoloration was apparent around the periphery of the burned area (about 2×2 inches). When the plastic seal was removed, it was found that the diameter of the drill hole had increased to about 10 mm. Furthermore, the eschar tissue could easily be lifted away from the viable tissue with little or no bleeding. The experiment was repeated several times with both lyophilized and acetone precipitated material in undiluted powdered form and in various carriers such as physiological saline, vanishing cream and agar and with substantially identical results.

In the absence of the 1 mm hole or the needle punctures referred to above, the action of the mixture is somewhat slower and the eschar tissue more completely digested. It appears that the proteolytic activity carries the escharase to the interfacial tissue, and the latter is hydrolyzed by the escharase.

What has been described thus far is a water soluble proteolytic enzyme mixture in which the molecular weight of the components is from about 30,000 to 50,000 dalton. It is activated by moisture, and is reasonably stable in the presence of moisture. However, if exposed to a moist atmosphere for an extended period of time, say for example a day or more, it is subject to autodigestion with loss of activity. The mixture also loses its proteolytic activity when exposed to a temperature of 100° Celsius for about five minutes. It is therefore heat labile.

The mixture contains escharase. Escharase is a water soluble, heat labile proteinaceous material, free of caseinolytic activity. Its peak isoelectric point is about 6 and generally ranges from about 5.85 to 6.10. The protein is comprised of at least two and most likely three subunits, each of which has a molecular weight from about 14,300 to 15,000 daltons. There is a characteristic absorption peak in the ultraviolet region of the spectrum at 280 nm. A characteristic of the products of the invention is their hydrolytic activity, even in the absence of sulfhydryl activation or the presence of sulfhydryl deactivating quantities of phenylmercuric acetate.

The proteolytic enzyme mixture of this invention containing the escharase, or escharase itself can be used to treat burn patients and produce graftable beds in accordance with the procedures described and illustrated above. They can be used in the free state or in the form of physiologically acceptable alkali metal and acid addition salts. The salts can be prepared by reaction in an aqueous medium between the hydrolytic enzyme substrate and preferably a slight molar excess of the selected dilute alkaline metal base or acid, normally a mineral acid or a low molecular weight aliphatic carboxylic acid. Typically useful bases include sodium and potassium hydroxide. Acids which can be employed include hydrochloric and acetic acids.

Escharase can be isolated from the proteolytic enzyme mixture obtained after expression through XM 50 Amicon Diaflo ultrafilter as described above.

In one isolation procedure, the enzyme mixture is subjected to molecular exclusion chromatography as a phenylmercuric salt (prepared by combining the mixture with an aqueous 0.2 M citrate buffer saturated with the sale in accordance with the procedure of Ota et al in Biochem. 3:180 (1960) on a column of Sephadex G 75. The elution of the enzyme product from this column preceded the elution of pure stem bromelain, and therefore must have a molecular weight in excess of bromelain, e.g. 32,000.

Sephadex G 75 is a polysaccharide gel available from Pharmacia of Upsala, Sweden. It is employed for molecular exclusion chromatography in accordance with procedures well known in the art.

The mixture obtained by exclusion chromatography is then fractionated by isoelectric focusing and subjected to polyacrylamide gel analytical electrophoresis in 1% sodium diodecyl sulfate (SDS).

For isoelectric focusing, the mixture was mixed in a sucrose gradient with LKB Ampholine amplylytes initially from pH 3 to 10, and subsequently at pH 5–8. The active material was concentrated at a peak isoelectric point of pH 6.04, with a range from 5.85 to 6.12. This isoelectric point is markedly different from that described for bromelain (pH 4.7 and 9.9). See Vestberg Acta.Chem.Scand 20:820 (1966).

LKB Ampholine is available from the LKB Company of Sweden for isoelectric focusing. It is believed to be a mixture of small ampholytes.

The products isolated by isoelectric focusing have an extremely high order of escharase activity.

For further purification, the isoelectric focused active material may be subjected to polyacrylamide gel electrophoresis at pH 9 in 1% SDS (Weber et al J.Viol.-Chem 244:4406 (1969). Only one protein staining band can be visualized with a measured electrophoretic mobility which, when compared with standard proteins of known molecular weight, evidences a molecular weight of between 14,300 and 15,000 daltons. Since SDS is known to dissociate proteins into their various subunits, if any, it is apparent that the escharase product of this invention comprises at least two, and most likely three, subunits of substantially the same molecular weight.

The material isolated from isoelectric focusing when subjected to ultraviolet spectrophotometry in water, exhibits a maximum absorption at 280 nm. This absorption is characteristic of aromatic amino acids.

From the foregoing studies it may be concluded that escharase is proteinaceous in nature and contains aromatic amino acids. It has been observed to be water soluble and heat labile. While the escharase products of the invention appear to be substantially pure by the procedures utilized, there are most likely small quantities of other materials still present.

The escharase products of the invention, as isolated by isoelectric focusing, were demonstrated to contain no caseinolytic activity when incubated under standard conditions with casein, in accordance with the procedure of Ota et al referred to hereinabove. Bromelain exhibits a high order of caseinolytic activity under these conditions.

The void volume from the G-75 Sephadex column chromatography described above which contained the hydrolytic escharase enzyme product also contained phenylmercuric acetate which inactivates sulfhydryl enzyme. The fact that this enzyme activity occurred in the presence of the mercuric compound indicates that, unlike bromelain, it does not require free sulfhydryl groups for its biological effect. However, it was found that when crude acetone precipitated bromelain was subjected to molecular ultrafiltration in the absence of thioglycolic acid (a sulfhydryl protector), the activity was substantially reduced, perhaps because of interaction between other molecules via their unprotected sulfhydryl groups with each other and the active molecule.

Escharase products of the invention can also be obtained by direct isoelectric focusing of the retentate of the material passed through the PM 30 filter described above. The isoelectric focusing is carried out by the procedures described above, and the products produced are substantially the same.

The various procedures for isolating active materials in accordance with this invention are summarized in the drawing.

Each of the fractions obtained in accordance with the foregoing procedures including the filtrate from the XM 50 Diaflo filter can be used to remove eschar tissue and produce graftable beds.

Eacharase and its salts can be used preferably when administered, as described above, through puncture holes in the nonviable tissue. When so used, the procedure is relatively fast. It will be apparent however that the escharase containing proteolytic mixtures obtained from any of STEPS A, B, C, D, or E will be less expensive to obtain than the substantially pure escharase obtained from STEPS F and H. The former products are preferred, especially when extremely rapid removal of the eschar tissue is not essential to the treatment of the patient. Of these, the mixtures obtained from STEPS C and D are preferred since they are relatively easy to obtain and of high activity.

It is clear that the fractions discovered herein are different from any previously reported materials. Moreover, unlike any previously reported materials they are safe, reliable and effective. The therapeutic results arising from proper utilization are predictable and reproducible.

The products can be used alone or in conjunction with the usual pharmaceutically acceptable, inert, stable excipients such as isotonic saline, polysaccharide gels, petrolatum or similar stable, inert hydrocarbon bases.

What is claimed is:

1. A method of dissecting and digesting devitalized tissue from a mammalian host which comprises contacting said tissue with an amount which is effective to hydrolyze said tissue so that said tissue can be removed from said host of a heat labile, water soluble proteolytic enzyme mixture obtainable from bromelain, said mixture containing escharase, a hydrolytic enzyme material free of caseinolytic activity with an isoelectric point of about 6, comprised of at least two subunits each of which has a molecular weight of from about 14,300 to 15,000 daltons, all of the components of the mixture having a molecular weight of from about 30,000 to 50,000 daltons.

2. A method as in claim 1 wherein treatment is effected while excluding oxygen.

3. A method of dissecting and digesting devitalized tissue from a mammalian host which comprises applying physiological saline soaks to the devitalized tissue to moisten it, and thereafter treating the moistened tissue with an amount which is effective to hydrolyze said tissue so that said tissue can be removed from said host, of a heat labile, water soluble proteolytic enzyme mixture obtainable from bromelain, said mixture containing escharase, a hydrolytic enzyme material free of caseinolytic activity with an isoelectric point of about 6, comprised of at least two subunits each of which as a molecular weight of from about 14,300 to 15,000 daltons, all of the components of the mixture having a molecular weight of from about 30,000 to 50,000 daltons.

4. A method as in claim 3 wherein treatment is effected while excluding oxygen.

5. A pharmaceutical composition comprising a heat labile, water soluble proteolytic enzyme mixture obtainable from bromelain, said mixture containing escharase, a hydrolytic enzyme material free of caseinolytic activity with an isoelectric point of about 6, comprised of at least two subunits each of which has a molecular weight of from about 14,3000 to 15,000 daltons, all of the components of the mixture having a molecular weight of from about 30,000 to 50,000 daltons.

6. A composition as in claim 5 wherein the pharmaceutically acceptable excipient is physiological saline.

7. A composition as in claim 6 wherein the weight ratio of enzyme mixture to physiological saline is 1:1.

* * * * *